(12) United States Patent
Liderfelt et al.

(10) Patent No.: US 10,760,041 B2
(45) Date of Patent: Sep. 1, 2020

(54) CELL CULTURE BAG WITH INTERNAL DIALYSIS MEMBRANE

(71) Applicant: GE Healthcare Bio-Sciences AB, Uppsala (SE)

(72) Inventors: Karl Liderfelt, Uppsala (SE); Eric Faldt, Uppsala (SE); Andreas Castan, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 739 days.

(21) Appl. No.: 14/915,808

(22) PCT Filed: Aug. 27, 2014

(86) PCT No.: PCT/SE2014/050979
§ 371 (c)(1),
(2) Date: Mar. 1, 2016

(87) PCT Pub. No.: WO2015/034416
PCT Pub. Date: Mar. 12, 2015

(65) Prior Publication Data
US 2016/0194589 A1 Jul. 7, 2016

(30) Foreign Application Priority Data

Sep. 6, 2013 (SE) ...................... 1351029

(51) Int. Cl.
*C12M 1/00* (2006.01)
*B01D 63/02* (2006.01)

(52) U.S. Cl.
CPC ............. *C12M 23/14* (2013.01); *B01D 63/02* (2013.01); *C12M 23/26* (2013.01); *C12M 23/34* (2013.01);
(Continued)

(58) Field of Classification Search
CPC .... B01D 2313/20; B01D 63/02; C12M 23/14; C12M 23/26; C12M 23/34; C12M 29/04; C12M 29/16
See application file for complete search history.

(56) References Cited

U.S. PATENT DOCUMENTS 3,969,190 A 7/1976 Hise et al.
5,576,211 A 11/1996 Falkenberg et al.
(Continued)

FOREIGN PATENT DOCUMENTS

DE 60026299 T2 8/2006
DE 20-2009-003681 U1 8/2009
(Continued)

OTHER PUBLICATIONS

International Search Report and Written Opinion regarding International Application No. PCT/SE2014/050979, dated Dec. 8, 2014, 11 pages.
(Continued)

*Primary Examiner* — Gautam Prakash
*Assistant Examiner* — Lydia Edwards
(74) *Attorney, Agent, or Firm* — Eversheds Sutherland (US) LLP

(57) ABSTRACT

The invention discloses a flexible bag for cell cultivation, comprising a cultivation compartment and at least one dialysis compartment, wherein the dialysis compartment(s) is/are delimited from the cultivation compartment by one or more dialysis membranes and is/are fluidically connected to a first and a second port in the bag.

16 Claims, 7 Drawing Sheets

(52) U.S. Cl.
CPC ............ *C12M 29/04* (2013.01); *C12M 29/16* (2013.01); *B01D 2313/20* (2013.01)

(56) References Cited

U.S. PATENT DOCUMENTS

| | | |
|---|---|---|
| 7,629,167 B2 | 12/2009 | Hodge et al. |
| 9,795,909 B2 | 10/2017 | Eriksson et al. |
| 2004/0110273 A1* | 6/2004 | Akers .................... C07K 14/47 435/283.1 |
| 2011/0213320 A1* | 9/2011 | Blott .................. A61M 1/0084 604/313 |
| 2013/0220907 A1* | 8/2013 | Fulkerson ........... A61M 1/1692 210/186 |
| 2014/0190876 A1* | 7/2014 | Meyer ................... A61M 1/284 210/87 |
| 2014/0287512 A1 | 9/2014 | Kaisermayer et al. |

FOREIGN PATENT DOCUMENTS

| | | |
|---|---|---|
| EP | 2527423 A1 | 11/2012 |
| WO | 2010025935 A1 | 3/2010 |
| WO | 2012/128703 A1 | 9/2012 |
| WO | 2012/158108 A1 | 11/2012 |

OTHER PUBLICATIONS

Portner R. et al., "Dialysis Cultures" In Appl Microbiol Biotechnol., 1998, vol. 50, No. 4, pp. 403-414,: abstract p. 404, col. 1, line 21-line 29; p. 404, col. 2, line 40-line 47, figures 2, 3.

Kasehagen C. et al, "Metabolism of hybridoma cells and antibody secretion at high cell densities in dialysis tubing," in Enzyme Microb. Technology, 1991, vol. 13, November, pp. 873-881.

European Search Report Received for European Patent Application No. 14841995.5, dated Mar. 2, 2017, 11 pages.

* cited by examiner

CELL CULTURE BAG WITH INTERNAL DIALYSIS MEMBRANE

CROSS-REFERENCE TO RELATED APPLICATIONS

This application is a filing under 35 U.S.C. 371 of international application number PCT/SE2014/050979, filed Aug. 27, 2014, which claims priority to Swedish application number SE 1351029-2, filed Sep. 6, 2013, the entire disclosures of each of which are hereby incorporated by reference.

TECHNICAL FIELD OF THE INVENTION

The present invention relates to cell culture bags, and more particularly to bags for dialysis cultivation of cells. The invention also relates to of method of dialysis cultivation of cells.

BACKGROUND OF THE INVENTION

The bio-processing industry has traditionally used stainless steel systems and piping in manufacturing processes for fermentation and cell cultivation. These devices are designed to be steam sterilized and reused. Cleaning and sterilization are however costly labour-intensive operations. Moreover, the installed cost of these traditional systems with the requisite piping and utilities is often prohibitive. Furthermore, these systems are typically designed for a specific process, and cannot be easily reconfigured for new applications. These limitations have led to adoption of a new approach over the last ten years—that of using plastic, single-use disposable bags and tubing, to replace the usual stainless steel tanks.

In particular bioreactors, traditionally made of stainless steel, have been replaced in many applications by disposable bags which are rocked to provide the necessary aeration and mixing necessary for cell culture. These single-use bags are typically provided sterile and eliminate the costly and time-consuming steps of cleaning and sterilization. The bags are designed to maintain a sterile environment during operation thereby minimizing the risk of contamination.

One of the successful disposable bioreactor systems uses a rocking table on to which a bioreactor bag is placed. The bioreactor bag is partially filled with liquid nutrient media and the desired cells. The table rocks the bag providing constant movement of the cells in the bag and also efficient gas exchange from the turbulent air-liquid surface. The bag, typically, has at least one gas supply tube for the introduction of air, carbon dioxide, nitrogen or oxygen, and at least one exhaust gas tube to allow for the removal of respired gases. Nutrients can be added through other tubes.

During cultivation, the cells produce metabolites, e.g. ammonium ions and lactate, which have an inhibitory effect on cells. This effect becomes an issue particularly in cultivation at high cell densities, which are required for cost-effective production of biopharmaceuticals such as therapeutic proteins or virus antigens. One way to reduce the concentrations of inhibitory metabolites is to use perfusion cultivation where culture medium is bled off by hydraulic flow through a filter which retains the cells but lets the metabolites and proteins pass through the filter. Expressed proteins can then be recovered from the filtrate and fresh culture medium is continuously supplied to the bioreactor to compensate for the lost liquid.

Due to the hydraulic flow through the filter, perfusion culture at high cell densities has issues with fouling and clogging of the filters. It is also in many cases desirable to retain the expressed protein in the bioreactor for recovery in a harvest step after cultivation. An attractive solution to these issues is to use dialysis cultivation, as described e.g. in R Poertner et al. Appl Microbiol Biotechnol (1998) 50: 403-414. Here, the cell culture is in contact with a dialysis membrane having a cut-off value chosen such that low molecular metabolites diffuse through the membrane, while cells and proteins are retained. There is no significant pressure drop over the membrane, meaning that mass transport is primarily by diffusion and little clogging or fouling will occur.

Dialysis cultivation is most commonly carried out with an external dialysis module, through which the culture is conveyed in a circuit outside the bioreactor. This is inconvenient as it increases the risks of a) contaminating the culture, b) leakage or catastrophic loss of the potentially biohazardous culture and c) attrition of sensitive cells by pumping through the circuit. Internal dialysis modules, placed inside the bioreactor have been described in e.g. Poertner, U.S. Pat. Nos. 5,576,211 and 6,933,144, but they are designed for rigid wall bioreactors such as stainless steel reactors or rolling bottles and the arrangements are not suitable for flexible bag bioreactors. They also tend to give low mass transport rates, which is detrimental to the process efficiency.

Accordingly there is a need for flexible bag bioreactors with internal dialysis modules suitable for dialysis cultivation with high mass transport rates.

SUMMARY OF THE INVENTION

One aspect of the invention is to provide a flexible bag suitable for dialysis cultivation without external dialysis modules. This is achieved with a bag as defined in claim 1.

One advantage is that the bag is suitable for dialysis cultivation in rocking bioreactors. Further advantages are that the bag provides for rapid mass transport during dialysis, that clogging of the membrane is avoided and the bag is easy to produce and to provide as a pre-sterilized disposable product.

A second aspect of the invention is to provide a bioreactor with a flexible bag, suitable for dialysis cultivation without external dialysis modules. This is achieved with a bioreactor as defined in the claims.

A third aspect of the invention is to provide a convenient method for dialysis cultivation. This is achieved with a method as defined in the claims.

Further suitable embodiments of the invention are described in the dependent claims.

DETAILED DESCRIPTION OF EMBODIMENTS

Figure 1:
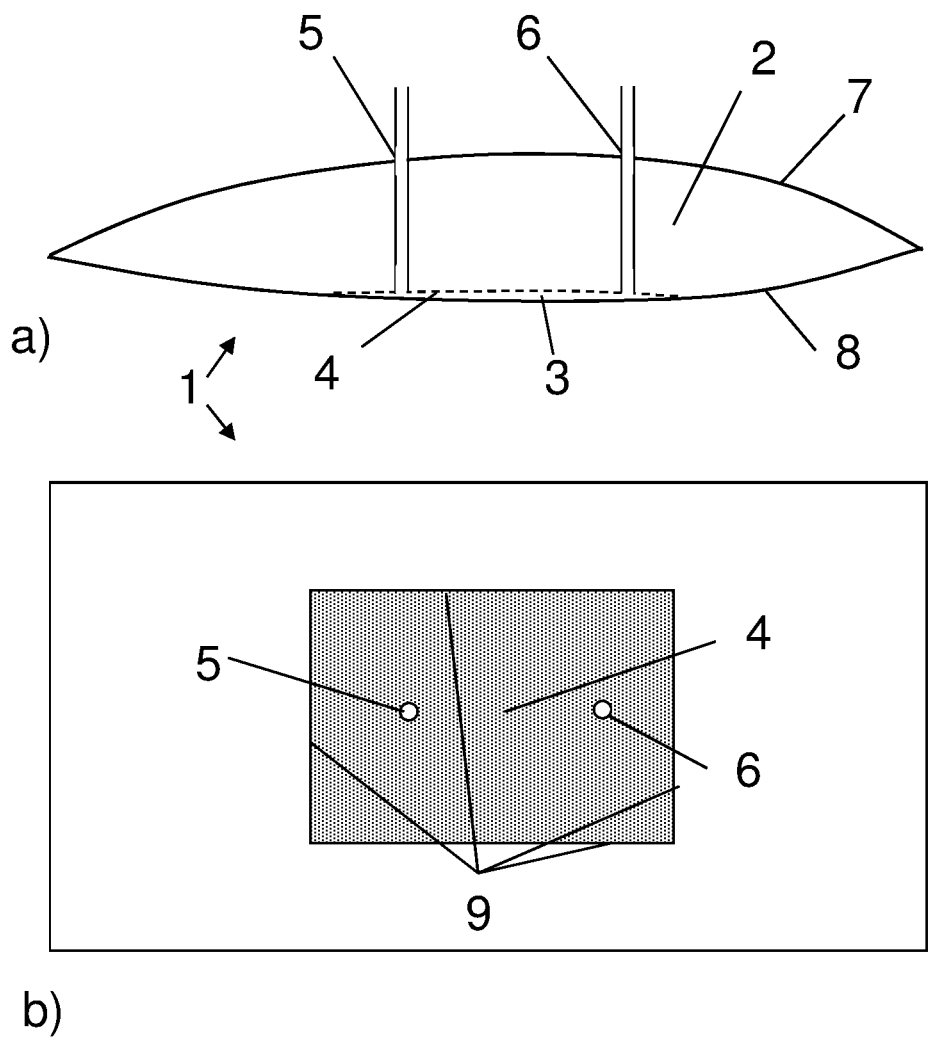
FIG. 1 shows a bag of the invention, with a dialysis compartment formed by a sheet of membrane fixed to an inner wall of the bag. a) Side view, b) Top view.

In one aspect, illustrated by FIGS. 1-6, the present invention discloses a flexible bag 1;11;21;31;41 for cell cultivation, which comprises a cultivation compartment 2;12;22;32;42 and at least one dialysis compartment 3;13;23;33;43. The bag can e.g. have a total volume of 0.5 l to 500 l, with the cultivation compartment e.g. having a volume of 0.3-495 l. The dialysis compartment(s) is/are delimited from the cultivation compartment by one or more dialysis membranes 4;14;24;34;44 and is/are fluidically connected to a first 5;15;25;35;45 and a second 6;16;26;36;46 port in the bag. The bag can have one or more walls, of which during cultivation one wall may be defined as the top wall 7;37;47 and another wall as the bottom wall 8;38;48. The first and second ports can be mounted in one or more of the walls, such as in the top wall, and via these ports liquid may be conveyed through the dialysis compartment from one port to the other. Alternatively, the ports may be mounted in one or more seams between two walls, such as in a seam joining the top wall with the bottom wall. The dialysis compartment(s) can be joined to one of the walls, such as the bottom wall, or it/they can be movable inside the bag. To increase the mass transport rate it can also be surrounded by the cultivation compartment. The dialysis membrane can suitably be an ultrafiltration (UF) membrane with a molecular weight (Mw) cutoff between 0.1 kDa and 1000 kDa, such as between 1 kDa and 100 kDa, between 1 kDa and 30 kDa or between 10 kDa and 100 kDa. To increase the mass transport rate it can be thin, such as with less than 0.2 mm or less than 0.1 mm thickness, and it may be produced from materials such as e.g. cellulose, polysulfones or polyethersulfones. It can be advantageous if the membrane material is compatible with gamma ray sterilization and/or is flexible enough to permit packaging and handling of the bag. It can also be advantageous if the entire dialysis compartment is flexible, in that flexing of the dialysis compartment caused by agitation in the cultivation compartment will then improve mass transport inside the dialysis compartment. The bag can be produced from a flexible plastic film or laminate, such as a film or laminate comprising polyethylene or an ethylene copolymer. It can e.g. be a pillow-type bag with a top wall and a bottom wall joined by heat-sealed seams, or it can be a three-dimensional bag with a top wall, a bottom wall and one or more side walls. In addition to the ports described above, the bag may comprise further ports for e.g. introduction of culture medium, cells, gases, nutrients, for removing samples and for various sensors. The fluidical connection between the dialysis compartment(s) and the first and second ports may e.g. be achieved by tubing or by having one or more dialysis compartments extending to one or more of the ports.

In some embodiments, the inner volume of the dialysis compartment or, if the bag comprises several dialysis compartments, the total inner volume of these compartments, is less than 10% of the volume of the cultivation compartment. It can even be less than 5% of the cultivation compartment volume, such as 0.01-5% or 0.1-2%. With a small dialysis compartment volume, a low flow rate of dialysis fluid is sufficient to maintain a high concentration gradient of metabolites over the membrane, which has an advantageous effect on the mass transport rate. Larger compartments require a higher flow rate, necessitating the use of larger volumes of dialysis fluid, which adds cost and the need for a larger pump.

In certain embodiments, the maximum thickness of the dialysis compartment or compartments is less than 2 cm, such as less than 1 cm, less than 2 mm, 0.5-10 mm or 0.5-2 mm. If the dialysis compartment is a pouch or other generally flat structure, the maximum thickness is measured as the maximum thickness of the compartment's inner volume during use conditions, If the dialysis compartment is tubular, the maximum thickness is defined as the maximum inner diameter of the tubular compartment during use conditions. A low maximum thickness provides for a high flow velocity of dialysis fluid, also at low to moderate flow rates. High flow velocities reduce the concentration polarization over the membrane and improve the mass transport rate.

Figure 2:
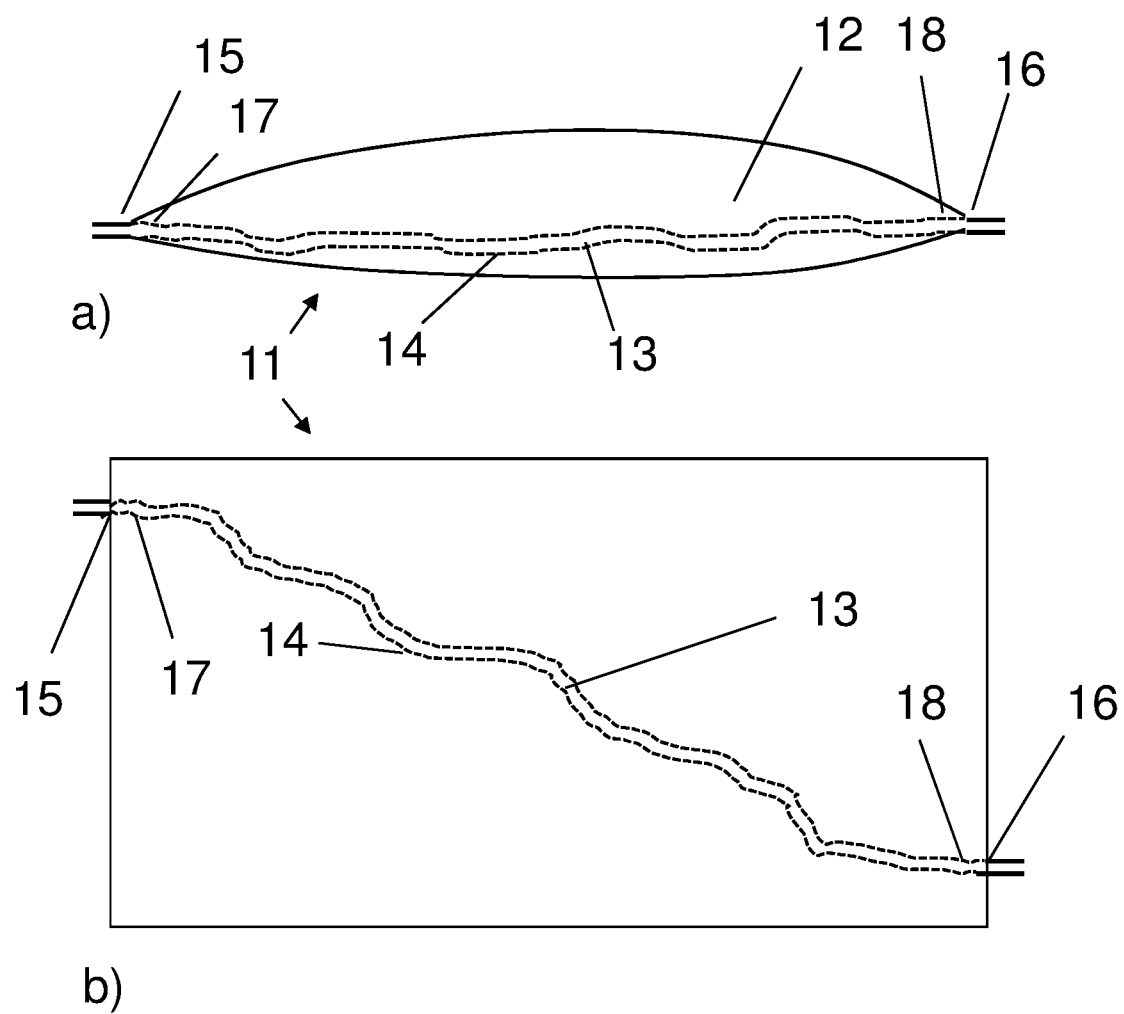
FIG. 2 shows a bag of the invention, with a dialysis compartment formed by a tubular membrane. a) Side view, b) Top view.
Figure 3:
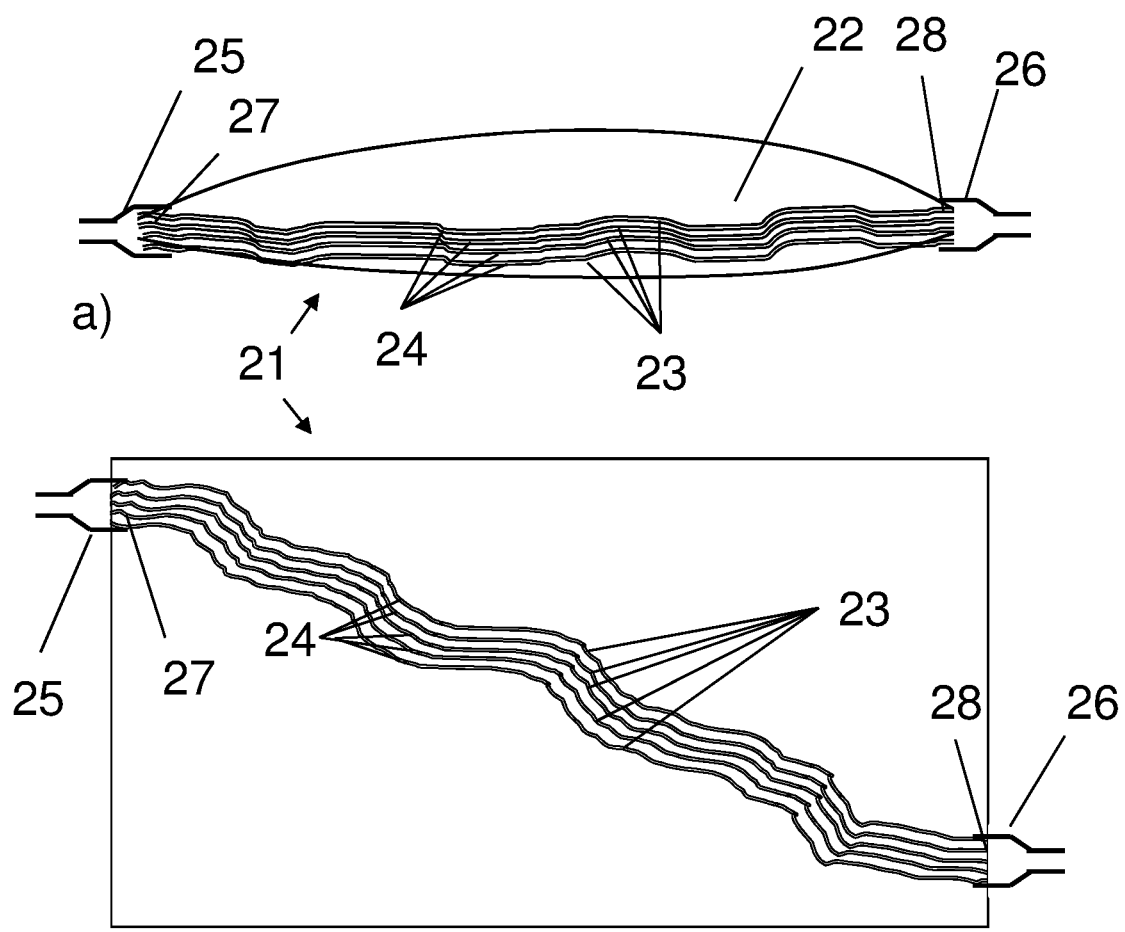
FIG. 3 shows a bag of the invention, with a plurality of dialysis compartments formed by a freely movable bundle of hollow fiber membranes. a) Side view, b) Top view.
Figure 4:
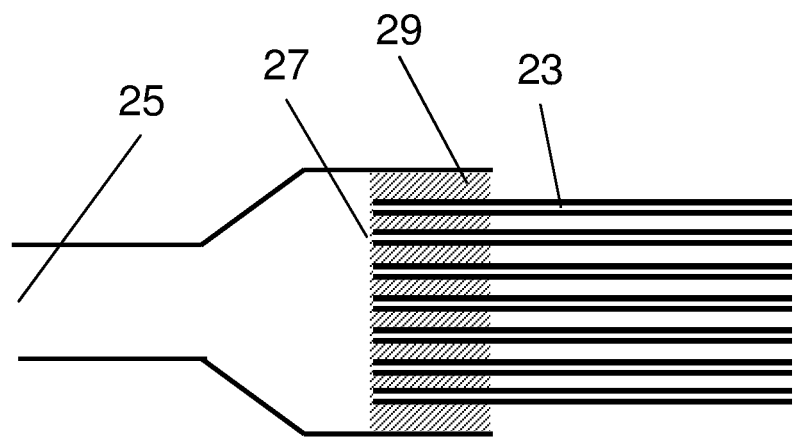
FIG. 4 shows an enlargement of one end of the hollow fiber bundle in FIG. 3.

In some embodiments, illustrated by FIGS. 2-4, the flexible bag comprises at least one tubular dialysis membrane 14;24 with a lumen 13;23, a first end 17;27 and a second end 18;28. The first end is fluidically connected to a first port 15;25 in the bag and the second end is fluidically connected to a second port 16;26 in the bag, such that the lumen 13;23 forms a dialysis compartment. The first and second port can e.g. be placed adjacent to two diagonally opposite corners of the bag to maximize the membrane length. The tubular membrane can be a length of cellulose dialysis tubing, available e.g. from Spectrum Laboratories, Inc. (USA), but it can also be a hollow fiber membrane (available e.g. from GE Healthcare Biosciences Corp., USA) or a tubular UF membrane such as e.g. PermaFlow (GE Power & Water, USA).

In certain embodiments, illustrated by FIGS. 3-4, the flexible bag comprises a bundle of hollow fiber membranes. Each individual hollow fiber membrane 24 has a lumen 23, a first end 27 and a second end 28, and for a plurality of the hollow fiber membranes each first end is fluidically connected to the first port 25, each second end is fluidically connected to the second port 26 and each lumen forms a dialysis compartment. This can be achieved by potting both ends of the fiber bundle with potting resin 29 (typically epoxy, polyurethane or silicone resin) in the same way as is normally done for hollow fiber cartridges, but with short pieces of tubing (or the port structure) at each end replacing the long tube normally used as a shell for cartridges, such that a major portion of the fiber length is open to the cultivation compartment but the lumens are only in fluid contact with the ports. The potting resin is arranged to seal the fiber ends such that only the lumens are in fluid contact with the ports. FIG. 4 shows a detailed view of a potted end of the bundle and its attachment to the port structure. The hollow fibers can be e.g. polysulfone hollow fibers (available e.g. from GE Healthcare Biosciences Corp., USA) or cellulose hollow fibers (available e.g. from Spectrum Laboratories, Inc., USA). They can also be braid-reinforced hollow fibers or other types of fiber-reinforced hollow fibers, which minimize any risk for fiber breakage, particularly in very large scale applications, such as in bags with a total volume of 10-500 l or 25-500 l. In this case, the membrane layer can be spun on the outside of a fibrous hollow reinforcement braid, such that the hollow fiber has a cross section with the braid structure on the lumen side and the membrane layer outside the braid. The cut-off values can be as described above and the inner diameter of the membranes can be e.g. 0.4-1.5 mm, such as 0.4-0.8 mm or 0.4-0.6 mm. Smaller diameters provide for improved mass transport rates as discussed above in relation to dialysis compartment thickness and volume and the risk for clogging of the fibers is minimal as the dialysis liquid typically is a low viscosity particle-free aqueous solution.

In certain embodiments, illustrated by FIGS. 3-4, the flexible bag comprises a bundle of hollow fiber membranes, where each individual hollow fiber membrane 24 has a lumen 23, a first end 27 and a second end 28, wherein each of the first ends is fluidically connected to the first port 25, each of the second ends is fluidically connected to the second port 26 and each lumen forms a dialysis compartment. The discussion in the paragraph above also applies to this embodiment, which has the additional advantage that all the hollow fibers in the bundle are fluidically connected to both ports. This can be achieved by careful control of the potting process and rejection of any potted bundles containing closed fibers, using methods well known in the art of manufacturing hollow fiber cartridges.

In some embodiments, the tubular dialysis membrane and/or the hollow fiber membranes are arranged such that they are free to move in relation to the bag. Movement of the membrane(s) is advantageous as it reduces clogging/fouling of the membrane outside and it generally improves the mass transport rate. The ability to move can be achieved by not having any housing around the membrane(s) and by using membrane(s) with a length longer than the straight-line distance between the first and second ports in the bag during use conditions. The membrane(s) may e.g. have a length of 1.1-2 or 1.1-1.5 times the straight-line distance between the first and second ports.

In certain embodiments the tubular dialysis membrane and/or hollow fiber membranes are arranged directly in the cultivation compartment, i.e. without any constraint such as a housing or cage around the membrane(s). The absence of any housings, cage structures etc around the membrane(s) provides freedom of movement as described above and also provides unimpeded mass transport to the membrane(s).

Figure 5:
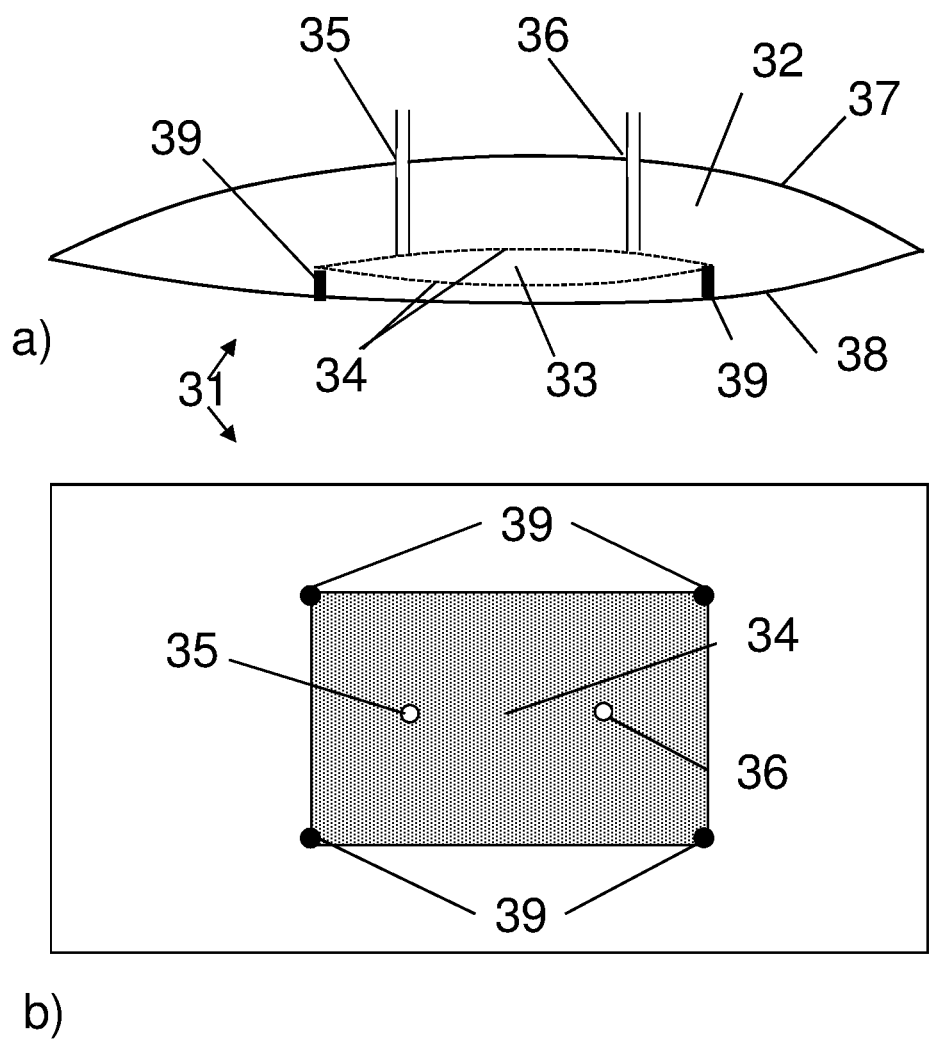
FIG. 5 shows a bag of the invention, with a dialysis compartment formed by a pouch attached to an inner wall of the bag. a) Side view, b) Top view.
Figure 6:
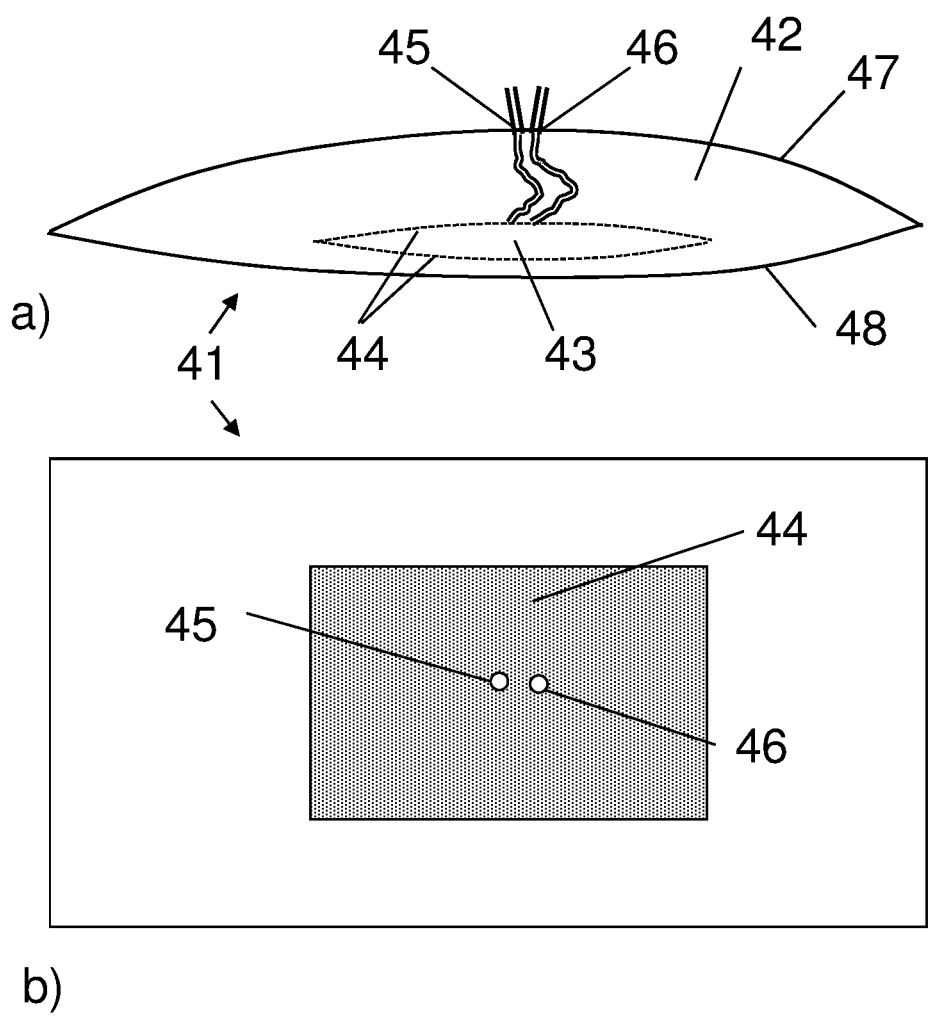
FIG. 6 shows shows a bag of the invention, with a dialysis compartment formed by a freely movable pouch. a) Side view, b) Top view.

In some embodiments, illustrated by FIGS. 1, 5 and 6, the dialysis compartment 3;33;43 is delimited from the cultivation compartment 2;32;42 by at least one sheet 4;34;44 of dialysis membrane. The dialysis compartment 3 can e.g. be formed by a sheet 4 of dialysis membrane attached along its edges 9 to an inner wall 8 of the bag. The fluidic connection to the bag ports 5,6 can then be achieved by two lengths of tubing connecting two ports in the membrane to the two bag ports. The dialysis compartment 33;43 can also be a pouch located inside the bag, in which case the pouch may e.g. be prepared from two sheets of membrane 34;44 with seams along the edges. The pouch can be attached to an inner wall 38 of the bag or it can be freely movable inside the bag. In the latter case, the pouch can suitably be arranged to have neutral buoyancy to prevent attrition of cells between the pouch and the bottom wall of the bag. To ensure free movement, the fluidic connection with the bag ports can be achieved by two lengths of highly flexible tubing connected to the bag ports and two ports in the pouch. The distance between the two ports in the pouch and the distance between the two bag ports can suitably be short (e.g. less than 10 cm or less than 5 cm) to facilitate free movement.

In certain embodiments, the flexible bag comprises one or more supports to prevent bulging of the dialysis compartment. Bulging is undesirable as it increases the maximum thickness of the dialysis compartment and it is advantageous to restrain the compartment with supports 39 or restrainer elements. The support(s)/restrainer element(s) 39 can comprise a coarse net or ribs which are mounted on the outside of the dialysis compartment. They can alternatively comprise internal joints between two inner walls of the dialysis compartment, typically two opposite walls. Such joints may be achieved e.g. by point-gluing or point-welding the walls directly to each other or by gluing or welding internal pillars to both walls.

In a second aspect the present invention discloses a bioreactor comprising the flexible bag as described above.

Figure 7:
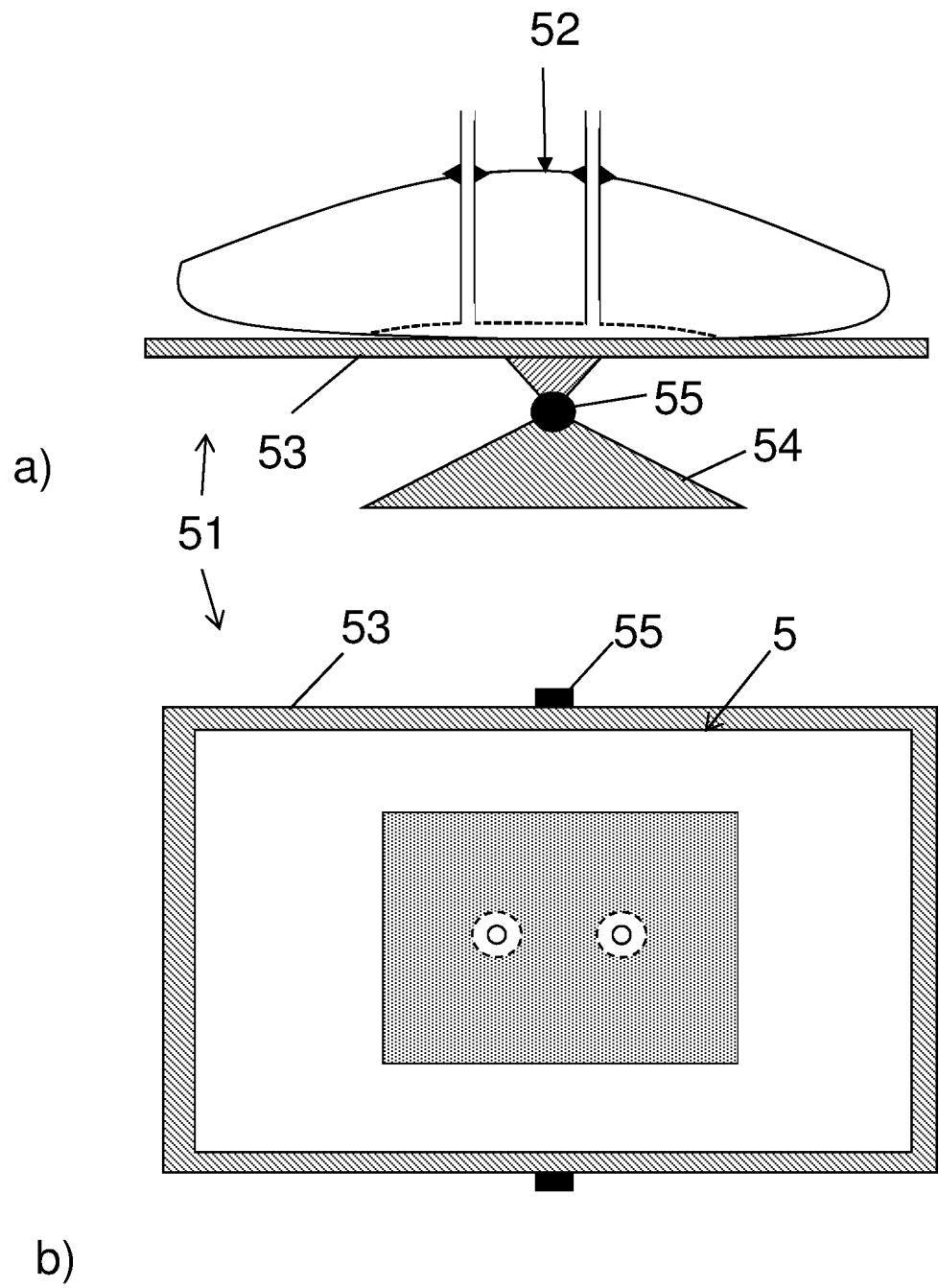
FIG. 7 shows a bioreactor of the invention, with the bag of FIG. 1 mounted on a pivotable support plate. a) Side view, b) Top view.

In some embodiments of the bioreactor 51, the flexible bag 52 is mounted on a support plate 53 which is pivotally mounted to a base 54 about a movable axis 55, as illustrated by FIG. 7. The support can typically be adapted to rock back and forth about the movable axis, with a controlled rocking rate and rocking angle, to provide agitation during cultivation.

In alternative embodiments, the bioreactor may comprise a generally cylindrical flexible bag mounted in a rigid support vessel. The bag can have a bottom wall, a top wall and a side wall (defined according to the directions during use), and may typically have an internal agitator, e.g. a magnetically driven agitator, to provide agitation during cultivation. In these embodiments, the dialysis compartment(s) can e.g. be fixed to the side wall.

In certain embodiments the bag of the embodiments described above is equipped with sanitary fittings and supplied presterilized, e.g. by gamma irradiation.

In certain embodiments the bioreactor further comprises cells and a cell culture medium. The cells can e.g. be mammalian cells, insect cells, bacterial cells, yeast cells etc. and they can be selected to express a product such as e.g. a protein. They can also be infected with a virus in order to produce virus particles suitable as antigens for vaccines or as gene therapy vectors.

In one aspect the present invention discloses a method of cultivating cells, which comprises the steps of:

a) Providing a flexible bag 1;11;21;31;41;52 comprising a cultivation compartment 2;12;22;32;42 and at least one dialysis compartment 3;13;23;33;43. The dialysis compartment(s) is/are delimited from the cultivation compartment by one or more dialysis membranes 4;14;24;34;44 and fluidically connected to a first 5;15;25;35;45 and a second 6;16;26;36;46 port in the bag.

b) Introducing cell culture media and cells in the cultivation compartment and cultivating the cells under agitation.

c) Flowing a dialysis liquid through the dialysis compartment(s) via the first and second ports to allow for mass transport of at least one component from the cultivation compartment via the dialysis membrane into the dialysis liquid. The pressure differential between the cultivation compartment and the dialysis compartment is less than 10 kPa and may even be less than 1 kPa or less than 0.1 kPa. The component transferred from the cultivation compartment to the dialysis compartment can e.g. be a metabolite such as lactate and/or ammonium ions. The dialysis liquid can e.g. be an aqueous buffer having a pH value and concentrations of salts and buffering components similar to the cell culture media in the cultivation compartment.

In certain embodiments of the method, the flexible bag is defined as above.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

All publications, patent publications, and patents are herein incorporated by reference to the same extent as if each individual publication or patent was specifically and individually indicated to be incorporated by reference.

The invention claimed is:

1. A flexible bag for cell cultivation, comprising:
   a) one or more walls;
   b) a cultivation compartment defined by the one or more walls;
   c) at least one dialysis compartment surrounded by the cultivation compartment, the at least one dialysis compartment being delimited from the cultivation compartment by at least one tubular dialysis membrane, wherein the at least one tubular dialysis membrane has a lumen, and two ends; and
   d) a first and second port, each port having one end extending through a wall of the flexible bag, and an opposite end fluidically connected to the ends of the at least one tubular dialysis membrane, wherein the lumen forms the at least one dialysis compartment, wherein the at least one tubular dialysis membrane does not have a housing around it and has a length longer than the straight-line distance between the first and second ports such that the tubular dialysis membrane is free to move in relation to the bag.

2. The flexible bag according to claim 1, wherein the total volume of the at least one dialysis compartment is less than 10% of the volume of the cultivation compartment.

3. The flexible bag according to claim 1, wherein the maximum thickness of the at least one dialysis compartment is less than 2 cm.

4. The flexible bag according to claim 1, further comprising a bundle of tubular dialysis membranes.

5. The flexible bag according to claim 1, wherein the at least one tubular dialysis membrane is a hollow fiber membrane.

6. The flexible bag according to claim 5, further comprising a bundle of hollow fiber membranes.

7. The flexible bag according to claim 1, wherein the at least one tubular dialysis membrane is arranged directly in the cultivation compartment.

8. The flexible bag according to claim 1, wherein the at least one tubular dialysis membrane has a length of 1.1-2 times the straight-line distance between the first and second ports.

9. The flexible bag according to claim 4, wherein the bundle of tubular dialysis membranes is reinforced with fibrous braids.

10. The flexible bag according to claim 3, wherein the maximum thickness of the at least one dialysis compartment is less than 1 cm.

11. The flexible bag according to claim 3, wherein the maximum thickness of the at least one dialysis compartment is less than 2 mm.

12. The flexible bag according to claim 8, wherein the at least one tubular dialysis membrane has a length 1.1-1.5 times the straight-line distance between the first and second ports.

13. A bioreactor comprising the flexible bag according claim 1.

14. The bioreactor according to claim 13, wherein the flexible bag is mounted on a support plate which is pivotally mounted to a base about a movable axis.

15. The bioreactor according to claim 13, further comprising cells and a cell culture medium.

16. A method of cultivating cells, comprising the steps of:
   a) providing the flexible bag for cell cultivation of claim 1,
   b) introducing cell culture media and cells in the cultivation compartment and cultivating the cells under agitation,
   c) flowing a dialysis liquid through the dialysis compartment(s) via the first and second ports to allow for mass transport of at least one component from the cultivation compartment via the dialysis membrane into the dialysis liquid, wherein the pressure differential between the cultivation compartment and the dialysis compartment is less than 10 kPa.

* * * * *